(12) United States Patent
Harrod, IV et al.

(10) Patent No.: US 10,475,320 B2
(45) Date of Patent: Nov. 12, 2019

(54) ADAPTIVE ROAMING ALGORITHM FOR A MOBILE PATIENT MONITORING DEVICE USING MOVEMENT CLASSIFICATION

(71) Applicant: KONINKLIJKE PHILIPS N.V., Eindhoven (NL)

(72) Inventors: John Price Harrod, IV, North Andover, MA (US); Brian Rosnov, Melrose, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/772,636

(22) PCT Filed: Nov. 9, 2016

(86) PCT No.: PCT/EP2016/077078
§ 371 (c)(1),
(2) Date: May 1, 2018

(87) PCT Pub. No.: WO2017/081057
PCT Pub. Date: May 18, 2017

(65) Prior Publication Data
US 2019/0130724 A1 May 2, 2019

Related U.S. Application Data

(60) Provisional application No. 62/254,450, filed on Nov. 12, 2015.

(51) Int. Cl.
*G08B 21/04* (2006.01)
*H04W 8/00* (2009.01)
(Continued)

(52) U.S. Cl.
CPC .......... *G08B 21/043* (2013.01); *G08B 3/10* (2013.01); *G08B 21/0423* (2013.01);
(Continued)

(58) Field of Classification Search
None
See application file for complete search history.

(56) References Cited

U.S. PATENT DOCUMENTS 8,135,380 B1 * 3/2012 Vargantwar ............. H04W 4/90
455/404.2
8,457,038 B1 6/2013 Xue
(Continued)

FOREIGN PATENT DOCUMENTS

WO 2010/004538 1/2010

*Primary Examiner* — Chico A Foxx

(57) ABSTRACT

A mobile patient monitoring device (10) includes a radio (14) having a scan threshold and a roam threshold that is lower or equal to than the scan threshold. The radio (14) is configured to scan to identify available access points when current access point power is below the scan threshold but above the roam threshold and roam to an available access point when current access point power is below the roam threshold. An accelerometer (12) is configured to measure acceleration. Device electronics (16) include at least one processor (24, 28) programmed to classify patient movement from the acceleration measured by the accelerometer and to assign values for the scan and the roam thresholds of the radio (14) based on the patient movement classification. Alternatively, the device electronics (16) may assign the values for the scan and the roam thresholds of the radio (14) based on received vital sign data acquired from an associated physiological sensor (32).

14 Claims, 2 Drawing Sheets

(51) Int. Cl.
*H04W 52/02* (2009.01)
*G08B 3/10* (2006.01)
*H04W 36/32* (2009.01)

(52) U.S. Cl.
CPC .......... *H04W 8/005* (2013.01); *H04W 36/32* (2013.01); *H04W 52/0206* (2013.01)

(56) References Cited

U.S. PATENT DOCUMENTS

| | | | |
|---|---|---|---|
| 2004/0172222 A1* | 9/2004 | Simpson | G06F 19/3418 702/189 |
| 2004/0199056 A1* | 10/2004 | Husemann | A61B 5/0002 600/300 |
| 2005/0138178 A1 | 6/2005 | Astarabadi | |
| 2005/0228300 A1* | 10/2005 | Jaime | A61B 5/0205 600/485 |
| 2006/0009698 A1* | 1/2006 | Banet | A61B 5/0205 600/485 |
| 2008/0222294 A1* | 9/2008 | Liang | H04W 36/24 709/227 |
| 2008/0285462 A1* | 11/2008 | Baker | H04W 16/18 370/241 |
| 2009/0063187 A1* | 3/2009 | Johnson | A61B 5/411 705/2 |
| 2010/0157864 A1 | 6/2010 | Salomone | |
| 2012/0108917 A1* | 5/2012 | Libbus | A61B 5/0006 600/301 |
| 2012/0170474 A1* | 7/2012 | Pekarske | A61B 5/002 370/252 |
| 2013/0150012 A1* | 6/2013 | Chhabra | H04W 48/16 455/418 |
| 2015/0106052 A1 | 4/2015 | Balakrishnan | |
| 2015/0148031 A1 | 5/2015 | He | |
| 2015/0170032 A1 | 6/2015 | Hodes | |
| 2016/0127958 A1* | 5/2016 | Viswanathan | H04W 8/06 370/331 |
| 2017/0078896 A1* | 3/2017 | Kephart, Jr. | H04L 41/0823 |
| 2018/0302189 A1* | 10/2018 | Harrod, IV | H04W 24/08 |

* cited by examiner

ADAPTIVE ROAMING ALGORITHM FOR A MOBILE PATIENT MONITORING DEVICE USING MOVEMENT CLASSIFICATION

CROSS REFERENCE TO RELATED APPLICATIONS

This application is the U.S. National Phase application under 35 U.S.C. § 371 of International Application No. PCT/EP2016/077078, filed Nov. 9, 2016, published as WO 2017/081057 on May 18, 2017, which claims the benefit of U.S. Provisional Patent Application No. 62/254,450 on Nov. 12, 2015. These applications are hereby incorporated by reference herein.

FIELD

The following relates generally to the medical monitoring and therapy arts, wireless patient monitoring art, and related arts.

BACKGROUND

Mobile patient monitoring devices (wearable or otherwise) allow patients to have a greater range of mobility. This can improve the quality of care as well as improve patient outcomes. To enable the acquired vital sign data to be monitored at a nurses' station or the like, the mobile patient monitoring device includes a radio providing wireless communication. To provide long battery life, the radio is preferably a short-range radio, which to achieve wider area coverage, communicates with a wireless network typically including access points (APs) distributed so as to provide complete coverage of the hospital floor or multiple hospital floors. The wireless network may, for example, be a WiFi network complying with IEEE 802.11 wireless communication standards. When the mobile patient monitoring device connects to the wireless network, it associates to an AP within the network. As a patient moves around the coverage area of the wireless network, the medical monitoring device's connection to the AP may become weak due to: (1) the distance between the AP and the device; (2) radio frequency (RF) interference between the AP and the device; (3) obstructions between the AP and the device (such as large metal objects, walls, or so forth). When the signal level becomes too low, the mobile patient monitoring device transfers, or "roams" to an available AP with higher power (typically nearer to the mobile patient monitoring device and/or having a less obstructed path to the mobile patient monitoring device). In order to identify available APs, the radio is further configured to scan for available APs and maintain an AP table listing available APs.

Generally, two thresholds of the radio of the mobile patient monitoring device can be configured to influence roaming behavior. The first threshold is a low signal strength scan threshold. When the signal strength of an AP drops below this value, the mobile patient monitoring device will start scanning the environment for available APs. This ensures that for a roam that is likely to happen, the AP table entries in the device are up-to-date. The second threshold is a low signal strength roam threshold. When the signal strength drops below this value, the medical monitoring device attempts to roam to another available AP with higher power.

The scan threshold is used to trigger a scan to update the AP table identifying available APs by signal strength and possibly other factors such as signal-to-noise ratio (SNR). The roam threshold is lower than the scan threshold, and the roam threshold triggers an actual switch (i.e. roam) to a new AP. This two-threshold design reduces radio power draw, since scanning the APs draws significant power.

The following discloses new and improved systems and methods that address the above referenced issues, and others.

SUMMARY

In one disclosed aspect, a mobile patient monitoring device includes a radio having a scan threshold and a roam threshold that is lower than the scan threshold. The radio is configured to: scan to identify available access points when current access point power is lower than or equal to the scan threshold but above the roam threshold; and roam to an available access point when current access point power is below the roam threshold. A three-dimensional accelerometer is configured to measure acceleration. Device electronics include at least one processor programmed to: receive vital sign data from at least one associated physiological sensor; classify patient movement from the acceleration measured by the 3D accelerometer; and assign or calculate values for the scan and the roam thresholds of the radio based at least on the patient movement classification.

In another disclosed aspect, a mobile patient monitoring includes a radio having a scan threshold and a roam threshold that is lower than the scan threshold. The radio is configured to: scan to identify available access points when current access point power is lower than or equal to the scan threshold but above the roam threshold; and roam to an available access point when current access point power is below the roam threshold. Device electronics include at least one processor that is programmed to: receive vital sign data from at least one associated physiological sensor; and assign or calculate values for the scan and the roam thresholds of the radio based at least on the received vital sign data.

In another disclosed aspect, a non-transitory storage medium storing instructions readable and executable by one or more microprocessors to perform operations including: receiving acquired vital sign data; operating a radio to scan to identify available access points when current access point power is lower than or equal to the scan threshold but above the roam threshold; operating the radio to roam to an available access point when current access point power is below the roam threshold; classifying patient movement from at least one of acceleration data sets received from a 3D accelerometer and access point power detected by the radio; and assigning values for the scan and the roam thresholds of the radio based on the patient movement classification.

One advantage resides in ensuring that a medical monitoring device is continuously connected to a network via an access point.

Another advantage resides in improved smoothness of transition between access point connections.

Another advantage resides in improved battery life of a medical monitoring device during times when the patient is stationary or in bed.

Another advantage resides in enhanced roaming performance and responsiveness when the patient being monitored by the mobile medical device has fallen or is experiencing a deteriorating physiological condition.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

Figure 1:
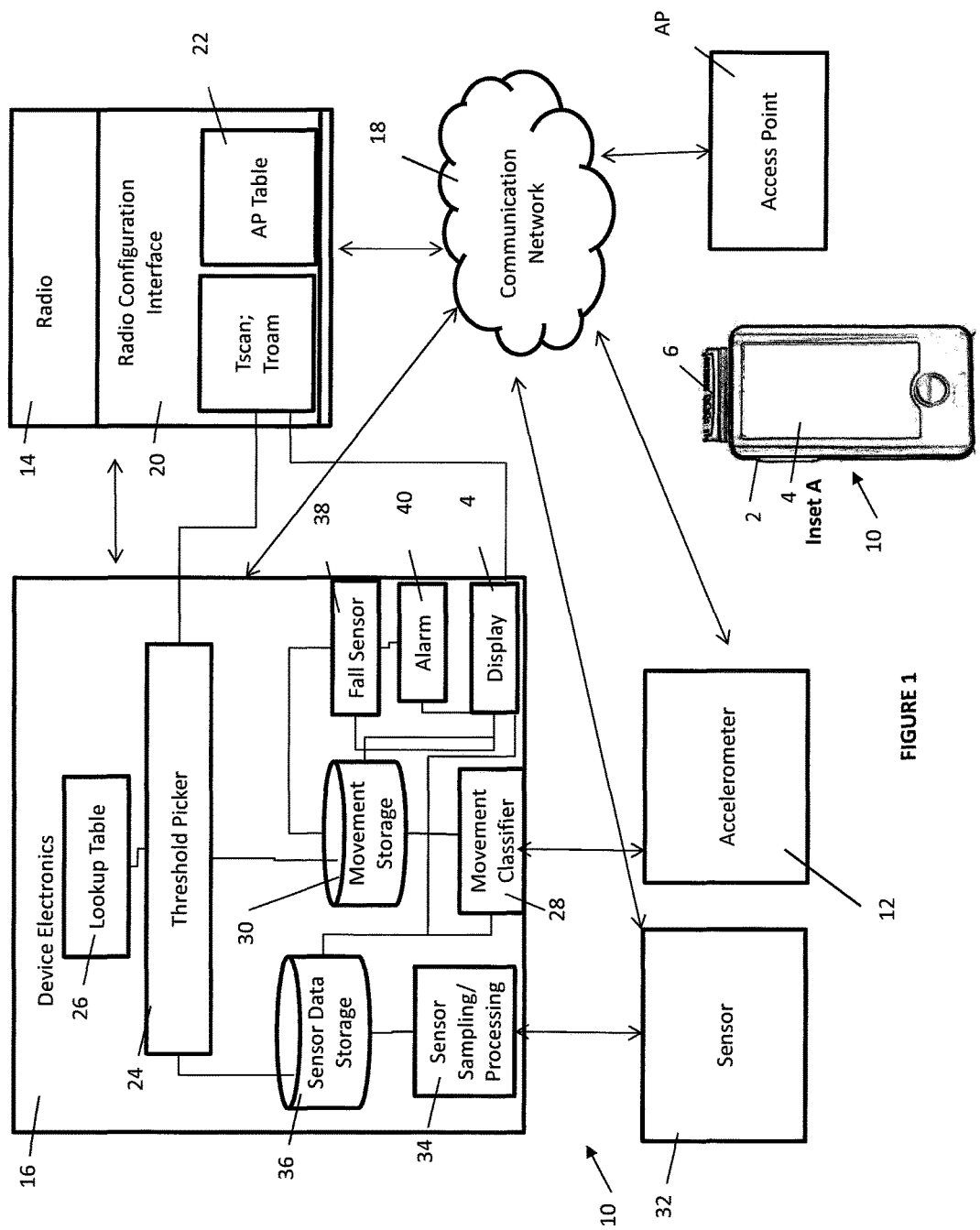
FIG. 1 illustrates a mobile patient monitoring device (Inset A) and the main drawing diagrammatically illustrates the mobile patient monitoring device as disclosed herein including diagrammatically indicated internal components such as device electronics and a radio.

Significant considerations in wireless mobile patient monitoring devices include battery life, and smoothness of transition between access points (APs) as the patient moves from the vicinity of one access point to the next, and communication reliability within the wireless system. The present disclosure is directed to an improvement which accrues to all these considerations, namely defining movement-based or patient condition-based scan and roam threshold values.

The idea behind the use of scan and roam thresholds is to trigger an AP scan only when the signal strength of the current AP is getting low, such that the probability is increasing that the roam threshold will be crossed. These scan and roam thresholds are typically set at the factory and are not user-configurable, however the thresholds and their distance of separation does have an impact on battery life and operating time due to the additional power required by the portable radio to scan for alternative APs.

The mobile patient monitoring device attempts to roam to an AP with better signal strength and less interference. In order to be ready to roam at any time, a medical monitoring device maintains the list of candidate APs to roam to in a roam table. Usually a mobile patient monitoring device roams to the AP in the roam table with the highest signal strength. The mobile patient monitoring device regularly scans the environment to make sure the APs and their signal strengths are up-to-date.

The scan threshold and a roam threshold are usually pre-programmed during the development phase of the mobile patient monitoring device, e.g. at the factory. In some designs, the scan and roam thresholds can be configured in the field, e.g. set on the device by a medical technician before it is put into use. Whether factory set or set in the field by a medical technician, this means that the two thresholds remain constant throughout the runtime of the device.

In improvements disclosed herein, the scan and roam thresholds are automatically updated to reflect environmental conditions such as the movement pattern of the patient. A feedback loop is provided so that the scan and roam thresholds are adapted to a patient's movement. In this way, the battery life of the mobile patient monitoring device is extended by cutting down on excessive AP scanning, while roam transitions are made smoother and have a lower failure rate.

In embodiments disclosed herein, the scan and roam thresholds are set based on patient movement classification. By way of illustration, if the movement is classified as "rolling on a gurney" the threshold ranges are set high so that AP scanning and roam events are triggered sooner (i.e. at a higher AP signal strength). This provides for nimble roaming appropriate for a patient being wheeled through the hospital corridors and likely to be crossing between AP zones. This nimbleness is achieved at the cost of higher power draw, but this is a favorable trade-off due to the high rate of movement of the patient. At the opposite end, if the movement is classified as "resting", e.g. in a bed or chair, then the threshold ranges can be set low, since the likelihood of a roam event is low. In all cases, the scan threshold is set higher than the roam threshold so that as current AP power drops the radio scans to update the AP table and then if it continues to drop and falls below the lower roam threshold the AP table is up-to-date for the roam event. In some cases, the change between the scan threshold and the roam threshold can be manipulated. For example, since the scan and roam thresholds are dynamically reconfigured, the relative change between the scan and roam thresholds is varied as well.

In some embodiments disclosed herein, in addition to patient movement, the scan and roam thresholds are also set based on clinical classification. In these embodiments, if the patient's vital signs (already monitored by the mobile patient monitoring device) are in normal ranges, then a delayed roam event is unlikely to lead to loss of critical data or prevent transmission of a critical alarm, and thus the threshold ranges can be set low to save energy. On the other hand, if a vital sign is reading abnormally, higher thresholds may be appropriate to increase reliability of waveform transfer and alarming.

With reference to FIG. 1, an exemplary embodiment of a mobile patient monitoring device 10 is shown. Starting with the Inset A, the mobile patient monitoring device 10 includes a housing 2, optionally with an integral display 4 for displaying current vital sign trend lines, device status indicators, or the like. A sensors port 6 is provided, via which one or more physiological sensors can be operatively connected. The patient monitoring device 10 may, for example, be a Philips Intellivue™ MX40 ambulatory patient monitor available from Koninklijke Philips N.V., Eindhoven, the Netherlands, or may be another commercial or custom-built patient monitoring device. The patient monitoring device 10 is mobile, so that it continues to monitor a patient from one location (i.e., the patient's hospital room) to another location (i.e., an examination room). For example, the Philips Intellivue™ MX40 is designed to be held in a pouch worn by the patient, or hung off the back of a wheelchair or so forth.

The main drawing of FIG. 1 diagrammatically illustrates internal components of the mobile patient monitoring device 10 of Inset A, along with illustrative physiological sensors that may be disposed inside the device housing 2 or operatively connected with the device 10 via the sensors port 6. The patient monitoring device 10 is configured to be in constant wireless communication with an associated access point AP to ensure a reliable, constant electronic communication link. In one example, the AP can be located in the patient's room, or alternatively, can be located outside of the patient's room at a suitable distance away to maintain a connection with the patient monitoring device 10. While one illustrative AP is shown, the hospital wireless network typically includes a number of APs strategically distributed over the hospital floor, or multiple hospital floors, to provide full area coverage of (at least) the areas the ambulatory patient is likely to visit. Optionally, APs may be located to provide coverage for some distance outside the hospital as well.

As shown in FIG. 1, the patient monitoring device includes a three-dimensional (3D) accelerometer 12, a radio 14, and device electronics 16. It will be appreciated that the accelerometer 12, the radio 14, and the device electronics 16 can be formed as separate units, or as one integral unit, of the patient monitoring device 10. In some embodiments, the radio 14 is an IEEE 802.11-compliant radio, although other types of radios configured for roaming are also contemplated. It will be appreciate that roaming could also involve 4G/LTE cells between towers or microcells in a building (i.e., APs may not be involved), BlueTooth Low Energy®, a Zigbee mesh cells, N number of nodes, and the like The radio 14 and the device electronics 16 are typically housed inside the device housing 2, while the 3D accelerometer 12 may be either an integral component housed inside the housing 2 or an external accelerometer operatively connected with the sensors port 6. If the accelerometer 12 is located inside the device housing 2, then it is configured to measure acceleration (i.e., along orthogonal directions designated without loss of generality as x-axis, y-axis, and z-axis, directions) of the patient monitoring device 10—and thus the built-in accelerometer measures motion of the patient wearing the patient monitoring device 10. Alternatively, if the accelerometer 12 is a separate component connected via an electrical cable to the sensors port 6, then the accelerometer is suitably directly attached to the patient and thereby measures patient movement. The accelerometer 12 can be any commercially-available accelerometer (i.e., an ADXL362 accelerometer, available from Analog Devices Inc., Norwood Mass.). The accelerometer 12 can be attached to any suitable portion of a patient (e.g., a chest, an arm, a leg, and the like) or housed inside the device housing 2. The accelerometer 12 continuously measures acceleration of the patient, e.g., during bedfast, chairfast, wheelchair movement, gurney movement, respiratory movement, and the like, and transmits this movement data to the device electronics 16. It will be appreciated that, instead of an accelerometer, any suitable Micro-Electro-Mechanical System (MEMS) device can by used, such as a gyroscope, a barometric pressure sensor, and the like.

The radio 14 is configured to monitor and maintain the connection between the patient monitoring device 10 and the AP via a network 18 (e.g., a wireless network, a local area network, a wide area network, a personal area network, the Internet, an intranet, a Philips proprietary ITS solution, a customer-supplied IEEE 802.11 wireless network, and the like). The radio 14 is configured to monitor and maintain the connection between the patient monitoring device 10 and the AP. To do so, the radio 14 includes a radio configuration interface 20 that stores a predefined scan threshold (shown in FIG. 1 as Tscan) and a predefined roam threshold (shown in FIG. 1 has Troam) that is less than or equal to the scan threshold. The radio 14 is configured to scan available APs when current AP power is below the scan threshold but above the roam threshold. As long as the connection strength (i.e., access point power, e.g. measured using Decibel-milliwatts, dBm in illustrative examples herein) between the patient monitoring device 10 and the AP is above the roam threshold, the connection there between is maintained and not severed. When the AP power falls below the scan threshold, the radio 14 scans for all available APs within a network (such as a hospital IP network). The scanned APs are stored within an AP table 22 of the radio configuration interface 20. Such scanning may thereafter be repeated at predefined time intervals as long as the AP power remains below the scan threshold. On the other hand, if the AP power falls further and passes below the roam threshold then the radio 14 switches to another available AP as indicated by the AP table.

In some embodiments, the device electronics 16 include a threshold picker 24 that is programmed to determine a level of each of the scan threshold and the roam threshold. These thresholds are preferably picked within some range, for example, the predefined roam threshold range may be between −64 dBm and −75 dBm inclusive, and the predefined scan threshold may be between −50 dBm and −65 dBm inclusive. The scan and roam thresholds for each patient movement classification may be stored in a lookup table 26, e.g. stored in an EPROM or other memory of the device electronics 16. The scan and roam thresholds can be initially set at default values which are transferred to the radio configuration interface 20 and stored therein. When the scan and roam threshold levels need to be adjusted based on patient movement or other environmental factors (as described in more detail below), the threshold picker 24 retrieves the updated scan and roam thresholds from the lookup table 26 and adjusts the threshold values of the radio 14 accordingly.

Each of the scan threshold and the roam threshold can be set (e.g., by a user, by a manufacturer, and the like) to be any suitable value. In one example, the scan threshold is −50 dBm and the roam threshold is −64 dBm. If the connection strength falls to −57 dBm, which is below the scan threshold, then the radio 14 scans the environment to detect available APs and to quantify the available APs by AP power and optionally other metrics such as signal-to-noise ratio (SNR), and the AP table is updated accordingly. It will be noted that the connection strength has not fallen below the roam threshold of −64 dBm at this point, so the radio 14 remains connected to the current AP. The connection strength can fall below the scan threshold for numerous reasons, including radio-frequency interference, an obstruction between the mobile patient monitoring device and the associated access point, and increasing distance between the radio and the AP due to patient movement.

If the connection strength between the radio 14 and the AP continues to fall until it is below roaming threshold of −64 dBm (in this example), then the radio 14 is configured to roam to another available AP that is identified from the AP table 22. Typically, the radio configuration interface 20 selects to roam to the AP in the AP table listed as having the strongest connection strength (i.e. largest AP power), although other factors such as SNR may be considered. Additionally, if the first-choice AP is unavailable (e.g. overloaded communicating with other devices), then a next-best AP in the AP table is chosen.

The threshold picker 24 is programmed to adjust the values of the scan threshold and the roam threshold based on environmental factors such as patient motion as measured by the accelerometer 12. In one example, the threshold picker 24 is programmed to adjust either the scan and/or the roam threshold level based on the type of patient movement. To do so, the device electronics 16 include a movement classifier 28 to classify the types of patient movement. The movement classifier 28 receives acceleration data from the accelerometer 12, and determines the current patient movement class from the acceleration data. For example, if the patient is bedfast or chairfast, the acceleration is essentially constant as a function of time, typically equal to the gravitational acceleration. If the patient is moving in a wheelchair, the acceleration will have some variability as a function of time due to the wheelchair accelerating and decelerating as the patient rolls the wheels. If the patient is lying in a gurney being moved by hospital personnel through the hospital corridors, the accelerometer data is likely to change frequently as a function of time as the gurney slows to accommodate traffic, speeds up when the aisle is clear, and turns around corners. Based on the measured acceleration as a function of time, the movement classifier 28 classifies the patient movement accordingly, e.g. a value of "1" for a bedfast movement, a value of "2" for a chairfast movement, a value of "3" for a wheelchair movement, and so on).

The movement classifier 28 transmits the patient movement classification to the threshold picker 24. From this patient movement classification, the threshold picker 24 is programmed to update the values for the scan and the roam thresholds of the radio 14 based on the patient movement classification. In some embodiments, the threshold picker 24 is programmed to assign or calculate the highest scan and roam thresholds for patient movement classifications corresponding to rapid patient movement and to assign or calculate a lowest scan and the roam thresholds for patient movement classifications corresponding to patient resting classifications. In doing so, the radio 14 can have stronger scan and roam thresholds during rapid movements (i.e., when the patient is being moved via a wheelchair or a gurney and, thus, passes multiple potential APs) and weaker scan and roam threshold during slow movements (i.e., during a bedfast or a respiratory movement, presumably when the patient is staying in the same room or moving to an adjacent room). Table 1 shows an example of a suitable embodiment of the lookup table 26 used by the threshold picker 24, where the first column ("Movement") is the patient movement classification determined by the movement classifier 28. (The last column, "Notes", is informational and is typically not contemplated for inclusion in the encoded lookup table 26). It will be appreciated that the range of values for the scan threshold and the roam threshold listed in Table 1 are for illustrative purposes only. The scan and roam thresholds can be set (e.g., by the user, the manufacturer, and the like) to any suitable level.

TABLE 1

| Movement | Low Signal Strength Scanning Threshold | Low Signal Strength Roaming Threshold | Notes |
|---|---|---|---|
| Bedfast | −65 dBm | −75 dBm | Patient is stationary. Save battery power by scanning less. Likely connected to the AP with the best signal strength. Only roam if connection is very poor. |
| Chairfast | −65 dBm | −75 dBm | Patient is stationary. Save battery power by scanning less. Likely connected to the AP with the best signal strength. Only roam if connection is very poor. |
| Walking | −57 dBm | −67 dBm | Patient is mobile and likely walking around the department. |
| Moving in a wheelchair | −50 dBm | −64 dBm | Possibly moving around the hospital at a faster pace. The client device needs to be more nimble and ready to roam from quickly fading APs. |
| Moving on a gurney | −50 dBm | −64 dBm | Possibly moving around the hospital at a faster pace. The client device needs to be more nimble and ready to roam from quickly fading APs. |

TABLE 1-continued

| Movement | Low Signal Strength Scanning Threshold | Low Signal Strength Roaming Threshold | Notes |
|---|---|---|---|
| Fall | −45 dBm | −55 dBm | Patient is likely in an unsafe situation and due to the fall may be laying on top of the monitoring device, severely attenuating the wireless connectivity |

For example, when the patient movement classification is "wheel chair movement" (a relatively rapid movement), the threshold picker 24 assigns a high −50 dBm value for the scan threshold and a high −64 dBm value for the roam threshold. Conversely, when the patient movement classification is "bedfast movement" (a slow movement or stationary), the threshold picker 24 assigns a low value of −65 dBm for the scan threshold and a low value of −75 dBm for the roam threshold. Advantageously, assigning or calculating the scan and roam threshold values based on the patient movement classification (1) extends the battery life of the device by cutting down on excessive low signal strength scanning and roaming; and (2) allows for smoother and more nibble roam transitions with a lower failure rate.

During normal operation, the mobile patient monitoring device 10 is connected with at least one physiological sensor 32 (e.g., a heart rate sensor, a respiratory sensor, and the like) via the sensors port 6 in order to receive vital sign data for the patient. Alternatively, the physiological sensor 32 can be operatively connected to the device 10 via a short-range wireless connection such as Bluetooth or integrated directly in the device 10 or device electronics 16. The physiological sensor 32 is configured to acquire vital sign data (e.g., heart rate, respiration rate, and the like). This data is transmitted from the physiological sensor 32 to a sensor sampler and processor 34 of the device electronics 16. The sensor sample and processor 34 optionally performs signal processing on the data (e.g., filtering, normalization, and the like), and then transfers this data to a sensor data storage 36 of the device electronics 16, and/or transmits the data to a nurses' station or other off-board device by way of wireless communication via the radio 14.

In some embodiments, the sensor data storage 36 is accessed by the threshold picker 24, which uses the sensor data, patient state information, and/or alarm state information to assess criticality of the wireless connection with the nurses' station or other off-board vital sign data recipient. The threshold picker 24 is programmed to assign or calculate the scan and the roam thresholds further based on acquired vital sign data, preferably choosing higher scan and roam thresholds if the vital sign data is physiologically abnormal, erratic, or otherwise indicates a possible incipient medical problem. For example, if the respiratory rate decreases and an alarm condition is indicated in the sensor data storage 36, this is information that is of high criticality to pass to the nurses' station; accordingly, the threshold picker 24 increases the scan and roam thresholds accordingly, as described above. That is, in these embodiments the threshold picker 24 is programmed to increase the scan and the roam thresholds responsive to abnormal vital sign data. In addition, the threshold picker 24 can be programmed to decrease the scan and the roam thresholds responsive to physiologically normal or stable received vital sign data. For example, when the respiratory rate is normal for an extended period of time (e.g., one hour, two hours, three hours, and the like), then the patient is considered stable. Accordingly, the threshold picker 24 decreases the scan and roam thresholds accordingly, as described above, so that the stable patient has the lowest scan and the roam thresholds for patient movement classifications corresponding to patient resting classifications, thereby allowing patients who are not considered stable to have increased scan and roam thresholds.

In the illustrative embodiment, acceleration data from the accelerometer 12 is used by the movement classifier 28 to classify the patient movement. In many cases acceleration is effective for this purpose. Various types of movement are expected to produce characteristic variations in the acceleration versus time, and these can be classified using suitable training data. To train patient movement classifier(s), acceleration data are collected for patients moving on gurneys, patients moving in wheelchairs, patients at bedrest or sitting in chairs or so forth. Each collected training acceleration data stream is labeled as to the actual patient motion, and the acceleration data stream may be processed to generate a representative feature vector. Suitable features may include, by way of non-limiting example: maximum acceleration magnitude over various time intervals; maximum acceleration in a directional component (e.g. x-direction) over various time intervals; acceleration variance over various time intervals; or so forth. These features are preferably chosen to be probative of the patient motion and efficient to compute. The resulting training data (features sets each labeled by the actual patient motion) are used to train a patient movement classifier, or a set of patient movement classifiers (e.g. a binary classifier to determine whether the patient is at rest, a binary classifier to determine whether the patient is moving on a gurney, etc).

The trained classifiers are then applied by the movement classifier 28. In this inference phase, acceleration data as a function of time are collected by the accelerometer 12. The chosen features are computed for the acceleration data and input to the trained classifier(s) which output the patient movement classification.

Advantageously, the accelerometer 12 can be used to perform other valuable tasks. For example, in some embodiments, the accelerometer 12 is in communication with a fall detector 38 implemented by the device electronics 16. The fall detector sensor 38 monitors the acceleration data stream to detect an acceleration event that is indicative of a patient fall (e.g., a sharp, brief acceleration). If the fall detector 38 detects a (possible) fall, then the fall detector 38 triggers an audio alarm 40 included in the device electronics 16. In addition, the device electronics 16 can also include the display 4 that shows a visual alarm for a patient fall. The patient fall alarm may also be wirelessly transmitted to the nurses' station via the radio 14. In addition, the display 4 can also display various information, such as: AP signal strength; (2) the type of patient movement; and (3) at least one patient parameter measured by a physiological sensor 32 (e.g. a vital sign trend line such as a heart rate trend line).

Figure 2:
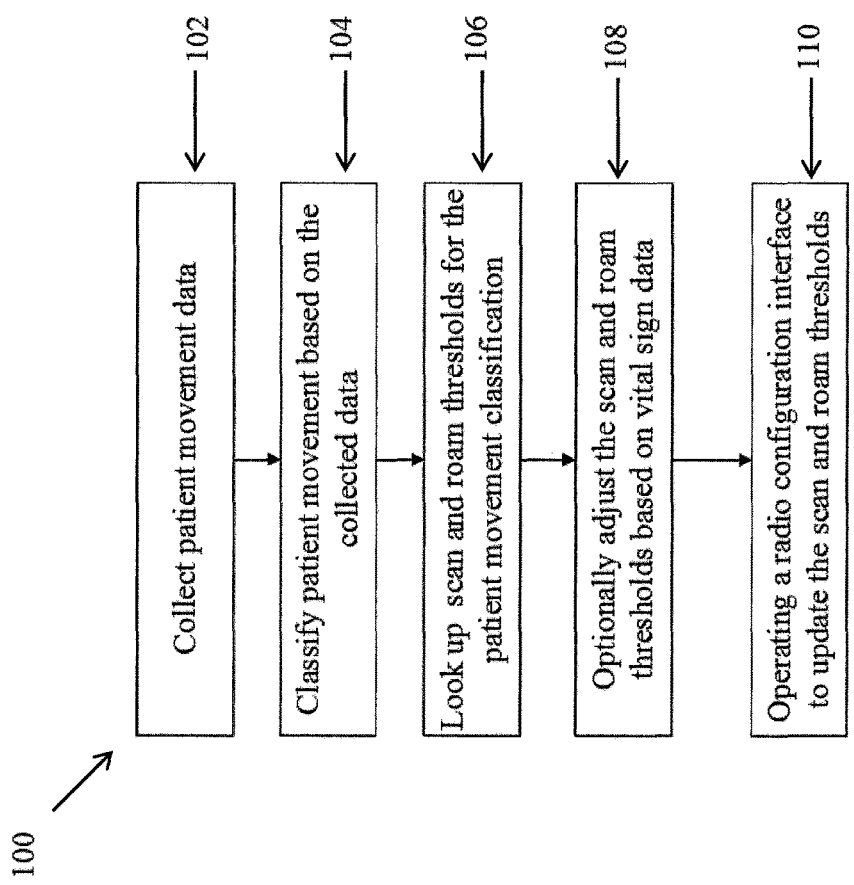
FIG. 2 is a flow chart showing an exemplary method of use for the device of FIG. 1.

FIG. 2 shows an exemplary flow chart of a method 100 of using the patient monitor 10. The method 100 includes the steps of: collecting data indicative of a patient movement (e.g. acceleration data) from the accelerometer 12 (Step 102); classifying patient movement based on the collected acceleration data (Step 104); looking up the appropriate scan and roam thresholds for the patient movement classification from the lookup table 26 (Step 106); optionally adjusting these scan and roam thresholds based on vital sign data (Step 108); and operating the radio configuration interface 20 to update the scan and roam thresholds of the radio 14 (Step 110).

In the illustrative examples, the patient movement classifier 28 operates on accelerometer data acquired by the accelerometer 12. This advantageously leverages an accelerometer that may be provided for another purpose such as fall detection. Further, it is generally feasible to assess the type (i.e. class) of patient movement based on acceleration data. However, in some cases acceleration on its own may be ineffective for assessing patient motion. For example, if the patient is on a very smoothly rolling gurney moving in a straight line down a straight hallway, then the acceleration experienced by the patient is essentially only gravitational acceleration, and it may be difficult to determine from this essentially constant acceleration that the patient is moving. Accordingly, in some embodiments another source of data for assessing the type (class) of patient motion may be used by the movement classifier 28. For example, the movement classifier 28 may additionally or alternatively assess patient movement based on the first derivative respective to time of the AP power. In this case, rapidly changing AP power (either increasing or decreasing) is indicative of rapid patient motion, while an essentially constant AP power indicates a patient at rest. In one example a current velocity of the gurney can be derived from past acceleration measurements. When the movement of the gurney is a steady velocity in the x-direction (with little acceleration in the y-direction and the z-direction), the movement classifier 28 determines that the patient is "rolling" (e.g., on a gurney, on a wheelchair, and the like).

The device electronics 16 are suitably implemented as a microprocessor programmed by firmware or software to perform the disclosed operations. To this end, the electronics may include components ancillary to the microprocessor such as data memory, a ROM, EPROM, FLASH memory, magnetic disk drive, or other non-transitory storage medium storing instructions readable and executable by the microprocessor to perform the disclosed functions, or so forth.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A mobile patient monitoring device, comprising:
   a radio having a scan threshold and a roam threshold that is lower than or equal to the scan threshold, the radio being configured to scan to identify available access points when current access point power is below the scan threshold but above the roam threshold and roam to an available access point when current access point power is below the roam threshold; and
   device electronics including at least one processor programmed to receive vital sign data from at least one associated physiological sensor, assign values for the scan threshold and the roam threshold of the radio based at least on the received vital sign data, and update the scan threshold and the roam threshold calculated or stored in a lookup table listing the scan threshold and the roam threshold for different patient movement classifications based on the received vital sign data.

2. The mobile patient monitoring device according to claim 1, wherein the at least one processor is programmed to assign or calculate higher scan and roam thresholds for patient movement classifications corresponding to rapid patient movement and to assign or calculate lower scan and roam thresholds for patient movement classifications comprising patient resting classifications.

3. The mobile patient monitoring device according to claim 1, wherein the at least one processor is programmed to assign the scan threshold and the roam threshold further based on the received vital sign data.

4. The mobile patient monitoring device according to claim 1, wherein the at least one processor is programmed to increase the scan threshold and the roam threshold responsive to physiologically abnormal or erratic received vital sign data.

5. The mobile patient monitoring device according to claim 1, wherein the at least one processor is programmed to decrease the scan threshold and the roam threshold responsive to physiologically normal or stable received vital sign data.

6. The mobile patient monitoring device according to claim 1, wherein the at least one processor is programmed to generate an access points table including the available access points identified by a last scan, wherein the radio performs the roam by retrieving the available access points from the generated access points table.

7. The mobile patient monitoring device according to claim 1, wherein the at least one processor is further programmed to implement a fall sensor that detects a possible patient fall based on acceleration measured by a 3D accelerometer and generate at least one of an audio alarm in an alarm of the device electronics and a visual alarm on a display of the device electronics when the fall sensor detects the possible patient fall.

8. The mobile patient monitoring device according to claim 1 further comprising:
a housing including an integral display, wherein the radio, a 3D accelerometer, and the device electronics are housed inside the housing such that the mobile patient monitoring device is a unitary device and the 3D accelerometer measures acceleration of the mobile patient monitoring device; and
a sensors port via which the at least one associated physiological sensor operatively connects with the mobile patient monitoring device.

9. The mobile patient monitoring device according to claim 1 further comprising:
a housing including an integral display, wherein the radio and the device electronics are housed inside the housing such that the mobile patient monitoring device is a unitary device; and
a sensors port via which the at least one associated physiological sensor operatively connects with the mobile patient monitoring device; wherein a 3D accelerometer is a separate unit not disposed inside the housing and the 3D accelerometer operatively connects with the mobile patient monitoring device via the sensors port.

10. A non-transitory storage medium storing instructions readable and executable by one or more microprocessors to perform operations including:
receiving acquired vital sign data;
operating a radio to scan to identify available access points when current access point power is lower than or equal to a scan threshold but above a roam threshold;
operating the radio to roam to an available access point when current access point power is below the roam threshold;
classifying patient movement from at least one of acceleration data sets received from a 3D accelerometer and access point power detected by the radio; and
assigning values for the scan threshold and the roam threshold of the radio based on the patient movement classification, wherein at least one processor is configured to update the scan threshold and the roam threshold calculated or stored in a lookup table listing the scan threshold and the roam threshold for different patient movement classifications based on the received vital sign data.

11. The non-transitory storage medium according to claim 10, wherein the highest scan and roam thresholds are assigned for patient movement classifications corresponding to rapid patient movement or a fall and the lowest scan and roam thresholds are assigned for patient movement classifications corresponding to patient resting classifications.

12. The non-transitory storage medium according to claim 10, wherein the assigning includes increasing the scan threshold and the roam threshold responsive to abnormal vital sign data.

13. The non-transitory storage medium according to claim 10, wherein the assigning includes decreasing the scan threshold and the roam threshold responsive to physiologically normal or stable received vital sign data.

14. The non-transitory storage medium of claim 10, wherein the classifying comprises:
classifying patient movement from acceleration data received from the 3D accelerometer.

* * * * *